(12) United States Patent
Turpin et al.

(10) Patent No.: US 7,258,981 B2
(45) Date of Patent: Aug. 21, 2007

(54) SENSITIVE PROTEASOME SENSOR CONSTRUCTS AND METHODS FOR THEIR DESIGN AND USE

(75) Inventors: Pierre H. Turpin, San Francisco, CA (US); Yu Fang, Fremont, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 223 days.

(21) Appl. No.: 10/765,244

(22) Filed: Jan. 26, 2004

(65) Prior Publication Data

US 2004/0235015 A1   Nov. 25, 2004

Related U.S. Application Data

(60) Provisional application No. 60/442,377, filed on Jan. 24, 2003.

(51) Int. Cl.
*C12Q 1/68* (2006.01)

(52) U.S. Cl. .......................... 435/6; 435/325; 530/350; 536/23.4

(58) Field of Classification Search ...................... None
See application file for complete search history.

(56) References Cited

U.S. PATENT DOCUMENTS 6,183,776 B1    2/2001   Depui et al.
2002/0197676 A1* 12/2002   Lukyanov et al. ......... 435/69.1

FOREIGN PATENT DOCUMENTS

WO        WO 01/81427       11/2001

OTHER PUBLICATIONS

Li et al., The Journal of Biological Chemistry, vol. 273, 1998, pp. 34970-34975.*
Adams et al. "Proteasome Inhibitors: A Novel Class of Potent and Effective Antitumor Agents," Cancer Research (1999) 59:2615-2622.
Gurskaya et al. "GFP-Like Chromoproteins as a Source of Far-Red Fluorescent Proteins," FEBS Letters (2001) 507:16-20.
Rogers et al. "Amino Acid Sequences Common to Rapidly Degraded Proteins; The PEST Hypothesis," Science (1986) 23(4774):364-368.

* cited by examiner

*Primary Examiner*—James Ketter
(74) *Attorney, Agent, or Firm*—Bret E. Field; Bozicevic, Field & Francis LLP

(57) ABSTRACT

Provided are means and methods for sensing proteasome activity and other degradation pathways with a high level of sensitivity.

19 Claims, 8 Drawing Sheets

FIG. 1A

ZsProSensor-1

| ZsGreen1 wt | MODC (410-461) |

FIG. 1B atggcccagtccaagcacggcctgaccaaggagatgaccatgaagtaccgcatggagggctgcgtggatggccacaa
gttcgtgatcaccggcgagggcatcggctaccccttcaagggcaagcaggccatcaacctgtgcgtggtggagggcgg
ccccttgcccttcgccgaggacatcttgtccgccgccttcaactacggcaaccgcgtgttcaccgagtaccccaggacat
cgtcgactacttcaagaactcctgccccgccggctacacctgggaccgctccttcctgttcgaggacggcgccgtgtgcat
ctgcaacgccgacatcaccgtgagcgtggaggagaactgcatgtaccacgagtccaagttctacggcgtgaacttcccc
gccgacggccccgtgatgaagaagatgaccgacaactgggagccctcctgcgagaagatcatccccgtgcccaagca
gggcatcttgaagggcgacgtgagcatgtacctgctgctgaaggacggtggccgcttgcgctgccagttcgacaccgtgt
acaaggccaagtccgtgccccgcaagatgcccgactggcacttcatccagcacaagctgacccgcgaggaccgcagcg
acgccaagaaccagaagtggcacctgaccgagcacgccatcgcctccggctccgccttgccccgcggtcacggccaa
tgtggcaactcatgaaacagatccagagccatggcttcccgccggaggtggaggagcaggatgatggcacgctgccca
tgtcttgtgcccaggagagcgggatggaccgtcaccctgcagcctgtgcttctgctaggatcaatgtg Targeting of ZsGreen to degradation by the proteasome using motif from MODC.

Flow Cytometry. Mean Fluorescence Intensities (MFI) of HEK 293 cells transiently transfected with plasmids encoding ZsGreen, ZsGreend1 and ZsGreend410. Standard deviations from duplicates.

Flow Cytometry. Same as 1A. Cells were treated for 0 to 6 hours with 10 ug/ml ALLN.

FIG. 3A

Generation of stable cell clone expressing ZsGreend410 to monitor the activity of the proteasome in a HTS fashion.

Flow Cytometry. MFI of a stable clone of HEK 293 transfected with a plasmid encoding ZsGreend410. Cells treated for 6 hours with or without 10 ug/ml ALLN. Standard deviations from duplicates.

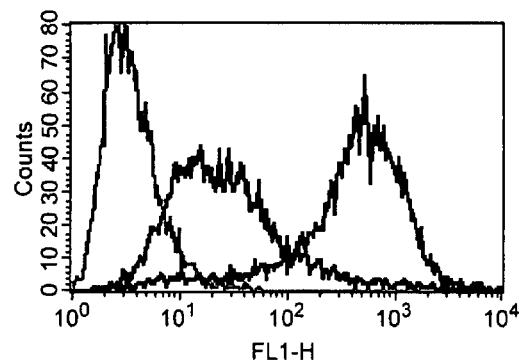

FIG. 3B

Microscopy. Micrographs of a stable clone of HEK 293 transfected with a plasmid encoding ZsGreend410. Cells treated for 10 hours with 10 ug/ml ALLN. Micrographs taken with same exposure times.

(same as 2B with the stable clone)

Dose response curve obtained with the stable clone and Acumen explorer machine. Compound 2=Lactacystin

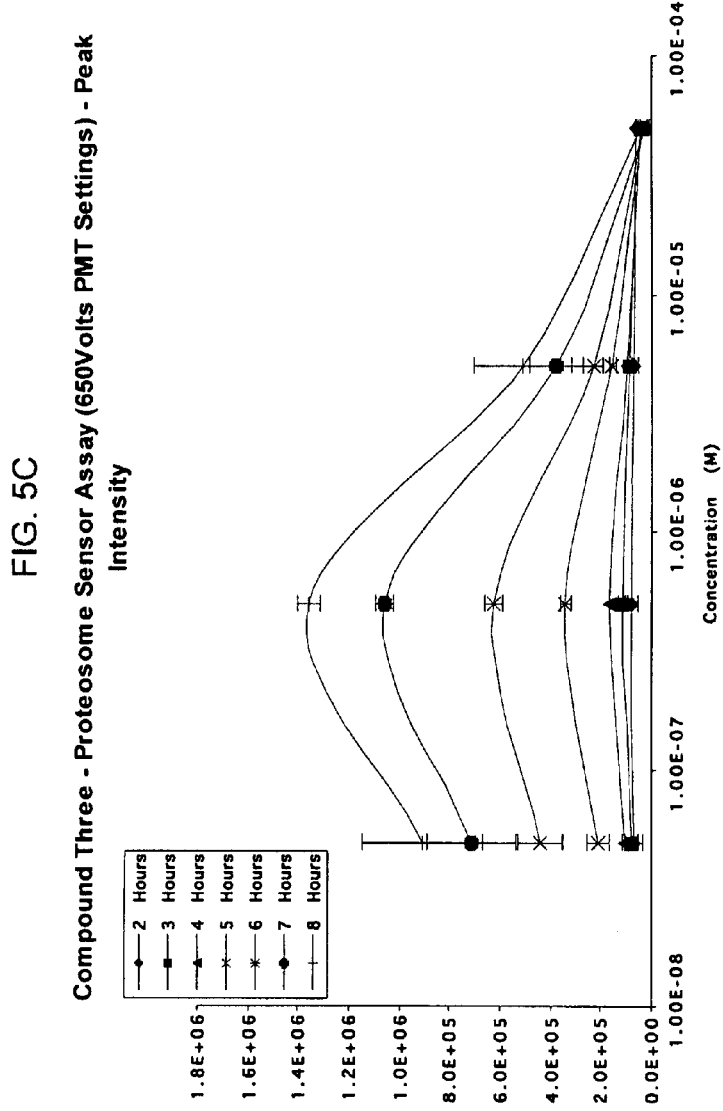

Dose response curve obtained with the stable clone and Acumen explorer machine. Compound 4=ALLN.

SEQUENCE LISTING

```
<160> NUMBER OF SEQ ID NOS: 1

<210> SEQ ID NO 1
<211> LENGTH: 855
<212> TYPE: DNA
<213> ORGANISM: Artificial Sequence
<220> FEATURE:
<223> OTHER INFORMATION: Synthetic Construct of sequence from Zoanthus
      sp.
      and mouse

<400> SEQUENCE: 1
atggcccagt ccaagcacgg cctgaccaag gagatgacca tgaagtaccg catggagggc        60
tgcgtggatg gccacaagtt cgtgatcacc ggcgagggca tcggctaccc cttcaagggc       120
aagcaggcca tcaacctgtg cgtggtggag ggcggcccct tgcccttcgc cgaggacatc       180
ttgtccgccg ccttcaacta cggcaaccgc gtgttcaccg agtaccccca ggacatcgtc       240
gactacttca agaactcctg ccccgccggc tacacctggg accgctcctt cctgttcgag       300
gacggcgccg tgtgcatctg caacgccgac atcaccgtga gcgtggagga gaactgcatg       360
taccacgagt ccaagttcta cggcgtgaac ttccccgccg acggccccgt gatgaagaag       420
```

-continued

```
atgaccgaca actgggagcc ctcctgcgag aagatcatcc ccgtgcccaa gcagggcatc    480
ttgaagggcg acgtgagcat gtacctgctg ctgaaggacg gtggccgctt gcgctgccag    540
ttcgacaccg tgtacaaggc caagtccgtg ccccgcaaga tgcccgactg gcacttcatc    600
cagcacaagc tgacccgcga ggaccgcagc gacgccaaga accagaagtg gcacctgacc    660
gagcacgcca tcgcctccgg ctccgccttg ccccgcggt cacggccaat gtggcaactc     720
atgaaacaga tccagagcca tggcttcccg ccggaggtgg aggagcagga tgatggcacg    780
ctgcccatgt cttgtgccca ggagagcggg atggaccgtc accctgcagc ctgtgcttct    840
gctaggatca atgtg                                                     855
```

SENSITIVE PROTEASOME SENSOR CONSTRUCTS AND METHODS FOR THEIR DESIGN AND USE

This application claims priority under 35 U.S.C. § 119(e) of provisional application Ser. No. 60/442,377, filed Jan. 24, 2003.

The field of this invention is proteasome function sensors and proteolytic pathways analysis.

BACKGROUND OF THE INVENTION

The Proteasome

The proteasome is a large, multi-protein complex present in both the cytoplasm and the nucleus of all eukaryotic cells. The 26s proteasome is involved in the constitutive and controlled degradation of proteins that control vital processes such as cell cycle progression, differentiation, and apoptosis. It also participates in the clearance of misfolded and damaged proteins and in the generation of peptides for MHC class I restricted antigen presentation (Schwarz et al, *Annual Review of Medicine.* 50:57–74 (1999). Recently, inhibition of the activity of the proteasome was observed in cells expressing aggregation-prone proteins, which are at the center of several neurodegenerative diseases (Bence et al. *Science.* 2001 May 25;292(5521):1552–5).

The diverse roles of proteasomal degradation place the proteasome at the core of pathological processes such as inflammation, autoimmunity, neurodegenerative diseases, and cancer. This key position in important pathological systems has motivated efforts to elucidate the mechanisms of action of the proteasome and to identify compounds to modulate its activity. Several inhibitors of the proteasome are now tested in clinical trials for cancer therapy (Adams, *Trends Mol Med.* 2002;8(4 Suppl):S49–54).

Proteins are identified for degradation by the proteasome via covalent modification with the small polypeptide ubiquitin or by sequence motifs in the target protein, which act as proteolytic signals (Schwarz *Annual Review of Medicine* 50:57–74,1999). One such motif, the PEST sequence, is found extensively in short-lived proteins (Rogers et al *Science.* 234(4774):364–8 1986). Mouse Ornithine DeCarboxylase (MODC) is one of the shortest half-lived proteins in mammals. The constitutive degradation of MODC by the proteasome is controlled by PEST sequences in its carboxy terminus (Loetscher et al. *J Biol. Chem.* 1991 Jun. 15;266 (17):11213–20; Ghoda et al *Mol Cell Biol.* 1992 May;12(5): 2178–85).

Proteomics

The study of proteasome function is also an important consideration in the emerging field of proteomics, the study of the proteins that are the gene products. A broad definition of proteomics is the effort to establish the identities, quantities, structures, and biochemical and cellular functions of all proteins in an organism, organ, or organelle, and how these properties vary in space, time, or physiological state.

As an example of immediate goals of the proteomics area of research is the Human Proteomics Initiative, which has as it goal annotating each know protein, providing information that includes the description of protein function, domain structure, subcellular location, post-translational modifications, splice variant, and similarities to other mammalian proteins.

A core need of proteomics efforts is to understand the cells specific protein degradation processes as these effect the levels and identities of proteins in the cell. Cellular levels of proteins will often vary substantially from the initial levels of productions due to degradation. Having a sensitive means of assessing the level of proteasome function in response to various factors would be of great value to this field of research.

Reporter Constructs

In monitoring biological systems, a number of reporter molecules have been usefully employed in tracking the cellular production and ultimate fate of a protein of interest by linking its genetic code to that of the reporter molecule. Then, when the reporter molecule is detected in the cell, this result indicates that the protein of interest is also present or not present. These reporters can include such molecules as luciferases among other reporters. However, the most widely used of these molecules are the fluorescent proteins, typically derived from marine animals, because currently they are the main source of non-invasively assessing the biological systems.

Fluorescent proteins are widely used as reporters for the detection of events in live cells. After the Green Fluorescent Protein (GFP and the enhanced EGFP) and its yellow (YFP) and cyan (CFP) variants, the discovery of the reef coral fluorescent proteins (RCFPs) ZsGreen, ZsYellow, AmCyan, AsRed (red), DsRed (orange-red) and HcRed (far-red) has expanded the spectrum of colors available for these studies (Matz et al., *Nat Biotechnol.* 1999 October;17(10):969–73; Gurskaya et al., *FEBS Lett.* 2001 Oct. 19;507(1): 16–20).

GFPs and RCFPs are stable proteins which, when they are produced accumulate in cells along with the protein of interest, allows easy detection of the movement and final degradation of that protein. The fusion of EGFP to amino acids 422 to 461 of MODC was shown to decreased the stability of EGFP(Li et al., *J Biol Chem.* 1998 Dec. 25;273 (52):34970–5). The vector encoding for the resulting fusion protein is marketed by BD Biosciences Clontech as d2EGFP. Several point mutations in the MODC sequence yielded an EGFP protein with an half-life of 50 minutes compared to 26 hours for the unmodified EGFP (Corish et al, *Protein Eng.* 1999 December;12(12):1035–40). The latter fusion protein was called d1EGFP. Clontech researchers used d1EGFP to analyze the regulation of gene expression in live cells (Li et al., 1998).

Proteasome Sensors

Researchers have exploited the fact that d2EGFP is targeted for proteasomal degradation to monitor the activity of the proteasome in live cells. Variations in the activity of the proteasome result in variation in the fluorescent signal of cells expressing d2EGFP (Andreatta et al., *Biotechniques.* 2001 March;30(3):656–60; Nahreini et al., *Cell Mol Neurobiol.* 2001 October;21(5):509–21). Other fusion proteins between GFP and proteasome targeting motifs have also been successfully used for this purpose (Bence et al. *Science.* 2001 May 25;292(5521):1552–5; Dantuma et al. *Nat Biotechnol.* 2000 May;18(5):538–43). Fluorescent sensors of the activity of the proteasome are to date the most powerful tools to monitor the activity of the proteasome.

The Dantuma group (Nature biotechnology (2000) vol 18 p538–543) constructed a fusion of GFP to Ubiquitin using a standard peptide bond on the N-terminus. The ubiquitination occurs during translation, producing a peptide bond. The sensitivity achieved is _4 µM Z-L3-VS and 60 µM NP-LLG-VS at 15 hours using flow cytometry (FACS).

The Bence group out of Stanford (Science (2001) vol 292 p1552–1555) designed a proteasome sensor construct which is a fusion of GFP to an artificial peptide, CL1, identified in yeast. The CR1 sequences was inserted in 3' of the reporter. The sensitivity achieved is 845 nM Lactacystin using flow cytometry.

The Andreatta group (Biotechniques (2001) vol 30 p656–660) has reported a construct designed from the fusion of GFP to a fragment of the Mouse Ornithine DeCarboxylase (MODC) protein. The sensitivity achieved is 2.5 uM Lactacystin and 2.5 uM MG132 at 20 hours using flow cytometry.

It would be an important advancement in the art to develop a sensor for proteasome activity with improved sensitivity, and other features to make available new, important areas of applications such as drug screening and analysis of the proteolytic systems of cells. Improvement of sensitivity of an order of magnitude or more over prior art systems would be of particular benefit.

SUMMARY OF THE INVENTION

A means and method of sensing proteasome activity and other protein degradation pathways with a high level of sensitivity are provided. The present invention allows for the first time the practical analyses for many applications of the activity of the proteasome and other proteolytic pathways using a reporter fused to a substrate of the proteasome.

The unexpected discoveries made during the development of preferred embodiments provides for the construction of a wide range of proteasome sensors with high sensitivity levels. The high sensitivities and other special advantages to the various embodiments of subject invention are required for a proteasome sensor which can function practically for several of the many of the new applications conceived by the inventor, as well as previously recognized potential applications.

In several preferred embodiments of the present invention, a class of fluorescent proteins previously considered unsuitable for use in a proteasome sensor was unexpectedly discovered to be highly advantageous in the analysis and monitoring of proteasome activity. In some cases, these newly recognized fluorescent proteins increase the sensitivity of systems employing standard fluorescent proteins by an order of magnitude or more.

Additionally, many of the inventive proteasome sensor constructs development and design features conceived by the inventor also provide substantial improvement in function and application, such as for sensitivity and stability. In some cases, these design features are geared towards providing a system closer to the naturally occurring protein degradation systems of cells, which contributes to the increased sensitivity.

The inventors have demonstrated the applicability of the many inventive features and aspects in as high a level system as mammalian cells, although simpler proteolysis systems in less developed organisms and microorganisms can also be monitored using constructs designed using the present inventive proteasome design strategies.

For higher order cell systems, the initially developed preferred embodiment of the present invention provides the first proteasome sensor using PEST sequences of a sensitivity adequate for practical, broad applications. The insights of the inventive concept are also critical in designing and constructing improved ubiquitin based systems, as described below.

An important advantage of the present invention is that the inventor has demonstrated its suitability for used using high throughput instrumentation, such as a 96 well plate reader. Other unique applications for the inventive constructs and methods are discussed below.

It is an object of the invention to provide means and methods to detect and quantitate the level of function of the proteasome, as well as analyze mechanisms of proteasome-dependent proteolysis or other proteolytic systems.

It is an additional object of the invention to providing a means and method for screening and selecting compounds which alter the activity of the proteasome, such as potential anti-cancer drugs.

It is a further object of the invention to provide one or more inventive sensors in cell lines to provide a multiplexed protein degradation pathway assay.

It is yet a further object of the invention to provide means and methods for screening for sequences within the genome that encode proteasome-targeting motifs.

BRIEF DESCRIPTION OF THE FIGURES

FIG. 1. (A) Map of ZsGreend d410.
(B) Sequence of ZsGreen d410 (SEQ ID NO:1).

DETAILED DESCRIPTION OF THE INVENTION

Figure 2A:
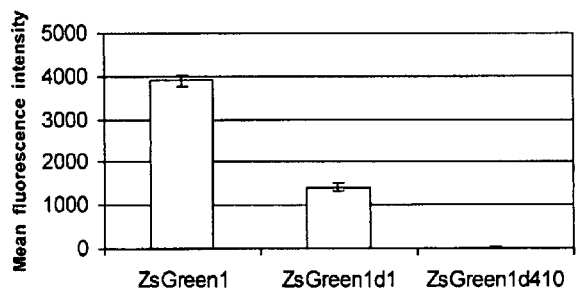
FIG. 2A ZsGreen-expressing cells fluorescent levels (transient transfection).

The present invention allows for the first time the analyses of the activity of the proteasome in many preferred applications. In one embodiment of the invention, levels of a naturally occurring substrate of the proteasome are monitored to assess the proteasome activity. The proteasome sensor construct may be a nucleic acid sequence which is delivered into the cell of interest, where it expresses the protein construct. Alternately, the protein construct may be delivered directly into the cell.

A major feature of the present invention is the optimization of the targeting element, in some cases through a "naturalization" approach to the construct design. Another major design feature of the present inventive proteasome sensor is the use of fluorescent reporters that are normally mediocre or unusable in other functional tests. Through this unexpected discovery, and the insight the inventor then achieved, a class of report proteins has been identified which are considerably more sensitive than standard reporters, in some cases by orders of magnitude.

The inventor has demonstrated the applicability of the invention in mammalian cells. While a preferred embodiment of the invention provides the first proteasome sensor using PEST sequences of sensitivity adequate for practical application, the insight of the invention also provides new ubiquitin based proteasome sensor systems and new ways of generating proteolytic markers. This broad applicability of the invention also allows monitoring of other protein degradation systems of the cells. An additional advantage of the present invention is that the inventors have demonstrated its suitability for used using a High throughput instrumentation, such as a 96 well plate reader.

In one embodiment of the invention, mammalian cells are transfected with the inventive plasmid. Under normal cell culture conditions, the fusion protein is rapidly degraded by the proteasome and the transfected cells show a reporting sequence, such as a fluorescence level, close to that of untransfected cells. In conditions under which the ability of the proteasome to degrade proteins is altered (e.g. drug screening for a compound that modulate the activity of the proteasome, or a particular cellular state) the reporter, such as ZsGreend410, is no longer degraded and the cells accumulate green fluorescence. As a result the reporter, such as ZsGreend410, serves as a "sensor" of the activity of the proteasome.

Naturalizing Elements

Several embodiments of the present invention uses a design approach which is divergent from prior proteasome sensors. These embodiments emphasize construction of the sensor, which more closely resembles the constructs produced by the cells during their natural protein degradation processes. These improvements produce increased sensitivity on their own, but also in some cases work synergistically with the improved fluorescent protein reporters of the present invention to provide a design with greater sensitivity than the additive advantage of each of the design features.

Several different factors will be considered in applying the "naturalization" approach of the present invention. This design approach starts with the selection or designing of a targeting component which is relatively close to the cellular system to be studied. By example, a proteasome targeting sequence is preferably selected that is present in a close parent of the organism studied. In one embodiment of the present invention, the inventor selected the PEST sequences from mouse for use in a proteasome sensor for human cells, rather then yeast sequences which have been chosen in previous researchers systems.

An other naturalization design factor to further optimize performance of a proteasome sensor is investigation of, and inclusion of, sequences surrounding the sequence involved in the degradation process per se. This design feature can elevate a sub-standard targeting component to an acceptable or even advantageous performance levels. Such additional inclusions can include about 1–100 aa additions to either or both side of the targeting sequence, with about 5–50 aa additions being the preferred range, and about 8–20 being the most preferred range.

As an example of the "broader reach" inventive design feature, Andreatta used aa 422–461 of MODC, which contain the PEST. However, it was unexpectedly found by the inventor that adding 12 residues n-ter of this sequence makes it more susceptible to proteasomal degradation, even without the presence of additional PEST.

In the case of ubiquitin, the inventive design features will take into account specific aspects of the ubiquitin system. For instance, a fusion protein between ubiquitin and the fluorescent reporter is not a fully natural reporter since ubiquitination normally occurs as a post-translational modification on lysines. In the discussion below, it is seen how the inventive design as developed by the inventor would allow a closer approximation to the natural system, exploiting the cells own mechanisms to optimize the resultant proteasome sensor.

Improvements to Targeting Sequence—MODC Exemplification

The inventive improvements in the MODC sequence discovered by the inventor produced the improvement of many times in the sensitivity of the PEST based proteasome sensor model. These findings have lead to a broader concept as to design and execution of proteasome sensor constructs which bring important insights into parallel protein degradation systems, such as ubiquitin systems.

In order to more fully understand the unexpected optimization of the MODC region of the inventive sensor by the inclusion of 12 additional upstream amino acids, the inventor studied the world literature on MODC, a mouse protein which is similar to the human structure.

The inventor found that there are two hypothetical PEST sequences reported in MODC, that is from aa 298–333 and from aa 423–449 (Rogers et al., 1986). Ghoda et al. (Science 1989 Mar. 17;243(4897):1493–5) were the first to show that the first sequence is not functional since cutting 37 aa from the c-terminal of MODC converts it to a stable protein although it still has the first sequence (the truncated protein is aa 1–423). Li and Coffino teach that aa 422–461 are necessary and sufficient for full degradation of MODC. (Li and Coffino, 1993).

On closer analysis and with the insight of the present invention, the inventor has as a theory that the Li data could be interpreted as supporting the inventive concept that the aa 376–461 region could also be a source of improved sensitivity. The aa 376–461 region contains the second PEST sequence and additional residues in c-terminal (449–461) and n-terminal (376–423). Therefore, it is an additional theory of the inventor that the aa 410–461 sequence is a better proteasome substrate than aa 422–461 (the one used in the d2EGFP system form Andreatta).

The inventor has demonstrated that by drawing on the encoded amino acids surrounding aa 422–461 central area, more efficient substrate of the proteasome can be generate. This may be due in part or in whole to the design of this construct being brought more closely to the naturally occurring construct.

The inventor's inventive naturalized proteasome sensor design represents a new approach in the art. For instance, the Dantuma group produced a construct which was a fusion of GFP to Ubiquitin using a normal peptide bond on the N-terminus. These artificial constructs differ substantially from Ubiquitin constructs, which are normally produced in the cell. Ubiquitination occurs on the lysine residues as a post-translational modification that requires the ubiquitination machinery (E1, E2s and E3s). While it would be difficult, and perhaps impractical, to fully reproduce the naturally occurring ubiquitination processes, the natural systems in the cell can be exploited to accomplish much of this goal post-translationally by the amino acid substitution scheme characterized in the description below of an NF-kB design.

Inventive Construct Design Approach

The inventive construct design criteria allows the practitioner to draw on publishes sources, as well as upon their own experimentation, to identify and select components that will be the most effective in providing a protein degradation monomer according to the subject invention.

By example, in designing a construct based on the proteasome pathway, the following criteria would be employed. The most promising candidate would be rich in proline (P), glutamic acid (E), serine (S) and threonine (T) (Rogers et al. Science, 1986. vol. 234 pp 364–368). To achieve this inventive approach, naturally occurring candidates would be screened, typically by a database searched, for those most rich in those amino acids. Such an approach could be augmented or supplanted by making substitutes in existing proteins, typically in non-critical areas, to include these preferred amino acids to elicit a strong cellular response to the target.

Exemplary PEST sequences: E1A (residues 44 to 49, 125–149, 177–202, 223–244), c-myc (10–51, 52–65, 83–126, 168–206, 206–241, 241–269, 276–287), p53 (39–62, 62–98, 213–232), c-Fos (31–91, 128–139, 205–250, 265–279, 307–358, 360–380), v-Myb (4–16, 174–186), p730 (323–361), HSP70 (3346, 125–152, 424–445), HMG-CoA reductase (381–395, 429–442, 442–456), TAT (382–395), alpha-casein (58–79, 151–193), beta-casein (1–25, 113–134) (Rogers et al. Science, 1986. vol. 234 pp 364–368) All the above sequences are likely sources of PEST sequences, which were identified by computer algorithm.

Other appropriate candidates would be targets of the ubiquitin pathway. Known targets of the ubiquitin pathway can be employed in the inventive design criteria, such as those in Adams (Trends Mol Med. 2002;8(4 Suppl):S49–54) among others. These choice can be improved as above, and artificial constructs base on common elements of natural targets can also be constructed.

Exemplary Ubiquitin targeting sequences: Cyclins A, B, D, E, CDK inhibitors, p53, c-fos, c-Jun, c-myc, N-myc, IkB, p130, cdc25 phosphatase, TAT, Topoisomerase I and IIalpha. (from Adams, Trends Mol Med. 2002;8(4 Suppl):S49–54).

Specific Exemplary Inventive Construct Designs

Inventive Design for Dantuma type system To demonstrate one embodiment of invention to provide an improved proteasome system using the subject inventive construct design method, the inventive concepts both of naturalization and optimization of reporter are demonstrated as applied to a Dantuma type system.

According to the subject invention, a Dantuma type system would be designed and constructed as follows. Sequences from IkBa that are target of the proteasome would be employed such as aa15–42 among other possibilities. IkBa needs phosphorylation on residues 32 and 36 to elicited natural ubiquitination of the construct by the cell.

One application of the inventive design approach would be to change those serines naturally occurring within the sequence into glutamic acid by mutation or through sequencing. This inventive design would serve to mimic the phosphorylation event which occurs naturally in the cell. This example of the inventive design would serve to constitutively target the protein to degradation.

Inventive Design for Bence type system The Bence group out of Stanford developed a fusion of GFP to an artificial peptide identified in yeast and called CL1. The following describes how an inventive construct using the design approach described herein would be developed from this know system.

The CL1 sequence is described in Gilon et al., (1998. EMBO Journal vol. 17 (10) pp 2759–66). The Gilon group was screening for genomic sequences from yeast. Because yeast is a lower eukaryote, as taught by the subject invention, such a system would be preferably naturalized by substituting a mouse sequence. This is because a mouse is a multicellular organism and a mammal, and so would mesh more appropriately with a mammalian cell line, such as human cell lines. The result would be that the so produced by the inventive design criteria would induce better targeting of the reporter protein to degradation by the proteasome.

The Gilon group identified the CL1 sequence. Because it is a genomic sequence, the inventor surmised that CL1 could fall into either a coding sequence or a non-coding sequence category. As a next step in the inventive construct design approach, the inventor ran a BLAST search with this sequence (a search on the NCBI). No match was found.

From this additional research, the inventor was able to determine that, since the yeast genome has been sequenced, the CL1 sequence is from yeast but highly unlikely to occur in a protein. It is more likely to have its origin from a promoter, an RNA, or other non-protein source. In line with the inventive design criteria, such a sequence would be considered less "natural", and would be a non-preferred sequence.

To show the application of the invention to provide and improved proteasome system, in the subject invention, the Bence system would be constructed with a sequence that normally occurs in mammalian cells, such as the mouse material above, with the improved aa sequences as described.

Inventive Design for Andreatta type system

Figure 5A:
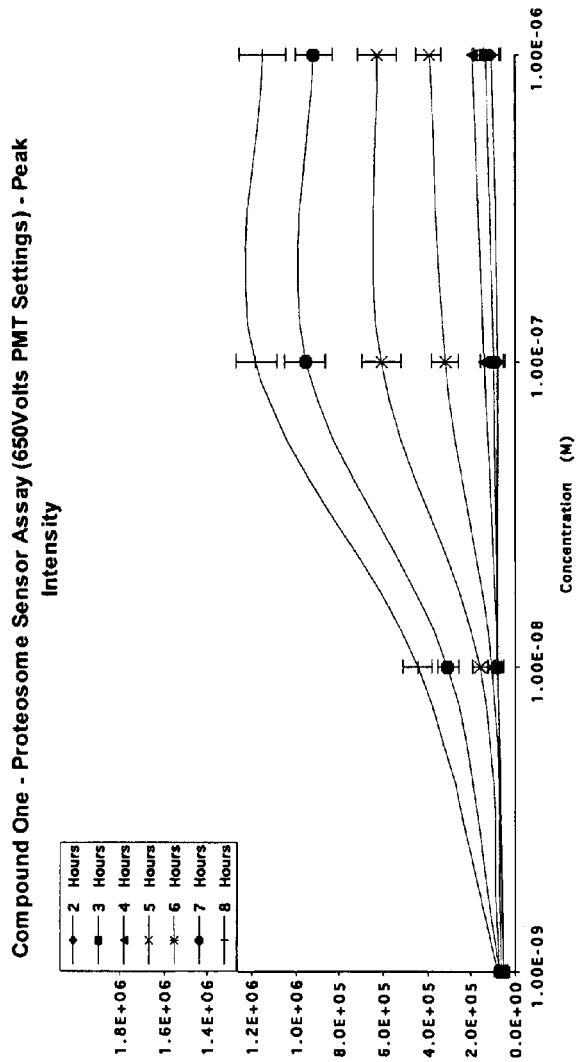
FIGS. 5A, B, C and D: dose response curves obtained with the Acumen Explorer machine (stable transfection).
Figure 5B:
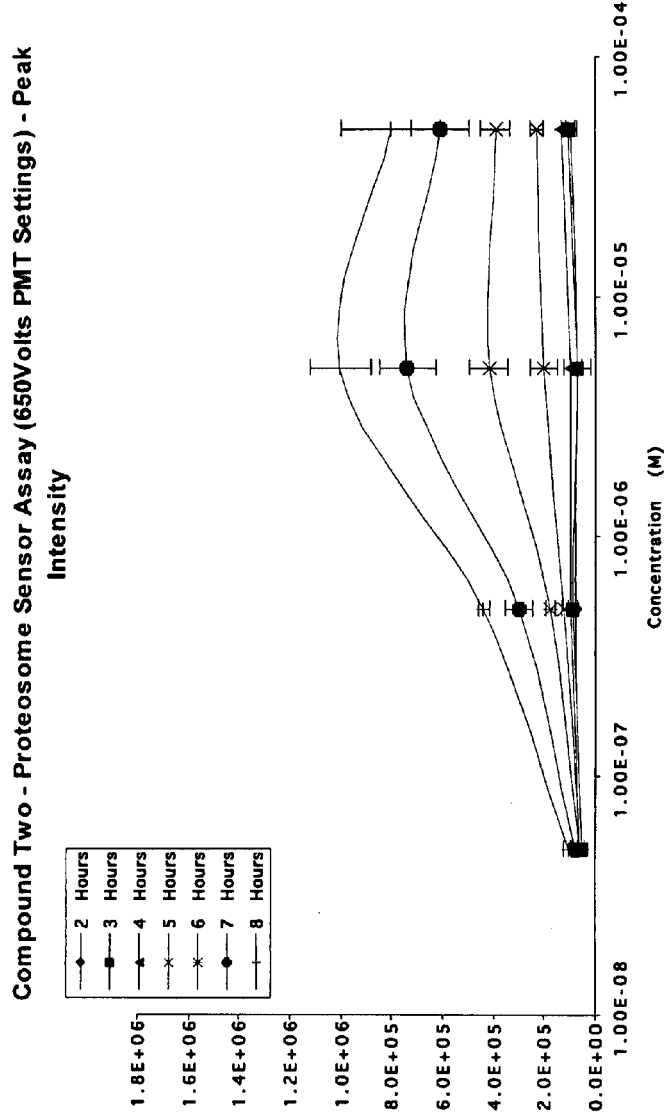
Figure 5D:
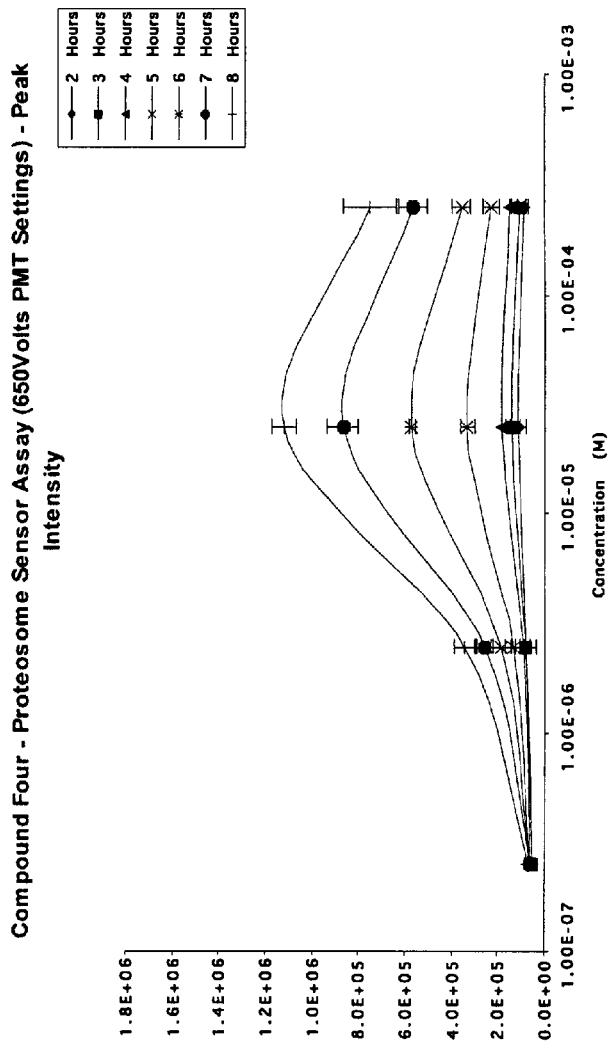

The Andreatta group has reported a construct designed from the fusion of GFP to a fragment of the Mouse Ornithine DeCarboxylase protein. In applying the inventive design strategies to the Andreatta system, the inventor noted that the d2 domain is a shorter version of the d410 domain. As taught by the concept developed as described above, the first 12 amino acids which occur before the d2 sequence were added to the construct. The result of this inventive embodiment was a construct with a sensitivity many times higher than that of the Andreatta construct, as seen in FIG. 5 below.

In one embodiment of the present invention, a plasmid vector encodes a fusion protein between a reporter molecule, such as the Reef Coral Fluorescent Protein ZsGreen, and a sequence which is subject to proteasome activity. In a preferred embodiment of the invention, one especially effective sequence subject to proteasome activity is that corresponding to amino acids 410 to 461 of Mouse Ornithine Decarboxylase (MODC). This sequence targets MODC for degradation by the prQteasome (Li and Coffino, 1993). Similarly, various other sequences subject can be employed. Note that, as set forth above, the surroundings of the sequence of interest would also be appropriate sources for the inventive design of the constructs.

Delivery Systems

The proteasome sensor construct is encoded by a nucleic acid sequence which is inserted into the cell. This may be done by its inclusion in a vector which is capable of transfecting a cell of interest. The entrance of the vector can be accomplished by a wide range of means well known to the practioner. Less preferably, the construct can be directly delivered into the cell of interest.

Once within the cell, the nucleic acid from of the construct expresses the protein construct. If a DNA, this nucleic acid with need to be transcribed by the cell into its constituent mRNA before it can be expressed. Alternately, and RNA construct can express the protein aspect of the construct directly.

Preferably, the DNA sequence of the construct would be transcribed into an RNA by the use of a strong promoter, such as the one found in the cytomegalo virus (CMV). Other features of the vector necessary for proper expression of the construct are well know in the practioner in the art. For instance, scientists normally include a poly A tail at the 3 prim end the construct to encourage mRNA production. Alternately, the protein construct may be expressed or otherwise constructed outside of the cell of interest, and then delivered directly into the cell by such means as microinjection or increasing the permeability of the cells, by example electroporation.

Reporter Molecules

A critical insight provided by the preferred embodiment of the present invention was the unexpected advantage of employing slowly maturing, destabilized reporters. These proteins are even more advantageous when they provide overproduction upon diminution of proteasome function. These inventively recognized report molecules, when included in the inventive proteasome sensor design, produces unexpectedly robust, sensitive proteasome sensor systems.

Identification and Study of Preferred Reporters

It is a theory of the inventor that dramatic increase in sensitive resulting from use of slowly maturing, destabilized reporters is due to the fluorescent background unexpectedly failing to increase with the overproduction of the protein. This is in contrast to standard fluorescent proteins function, and provided an opportunity for the inventor to consider the possible mechanism for this unexpected characteristic.

Figure 4:
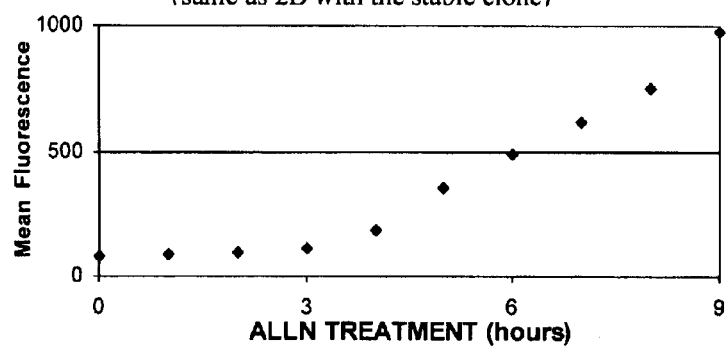
FIG. 4 ALLN treatment effect on fluorescence of the ZsGreend410-expressing clone (stable transfection). Note the delay in appearance of fluorescence.

As shown in FIG. 4, the profile for ZsGreen has this unexpected characteristic. As demonstrated by this data, when the clone is treated with ALLN, there is a delay of 3 hours before the appearance of fluorescence. This suggested to the inventor that that the fusion protein may have this unusual delay in fluorescent due to a distinctly slow maturation of the fluorophore. The ZsGreen employed by the inventor in the preferred embodiment was studied and determined to have a slow fluorophore formation compared to EGFP.

One theory of the inventor is that this slow maturation could contribute to, or be the primary determining factor, in the observed delay. The consequence of this theory is that the background fluorescence of cells not treated with proteasome inhibitors is low, even in cells that have high amounts of the protein.

The unexpected result is that cells that produce high levels of protein have a low background and would accumulate high levels of fluorescence upon treatment when subjected to proteasome inhibitors. Therefore the sensitivity of the inventive assays employing these slow to fluoresce, but heavy producing, reporter is high. This effect is highly pronounced in the example above since the cell clones were selected by the inventor with the highest fluorescence upon proteasome inhibition.

Using ZsGreend410 as an example, it is another theory of the inventor that this protein is degraded before it is fully expressed or is able to complete the folding which is a necessary prerequisite to becoming fluorescent. Because of this phenomena, there is very little baseline background. Therefore, cells, which produce high amounts of ZsGreend410 protein have low fluorescence in untreated conditions and very high fluorescence in treated conditions. We chose this type of cells during the generation of the stable clone.

Engineered plasmids encoding fusion proteins between ZsGreenwt and other proteasome-targeting motifs yield sensors of the proteasome that are more sensitive in general than the sensors using standard EGFPs. Therefore, application of the inventive construct designs to existing proteasome-targeting motifs previously described in the literature (Schwarz and Chiechanover, 2002; Bence et al., 2001; Dantuma et al., 2000 and references therein) will yield inventive constructs of high sensitivity.

Suitable reporter molecules for the purpose of the invention can be selected from the full gamete of reporter molecules, including fluorescent reporters. However, in accordance with the optimizing features of the presence inventive design criteria, florescent reporters should be selected or developed which demonstrate a delay of 1–20 hours before the appearance of fluorescence in the cell, preferably 1–6 hours, and most preferably 1–3 hours.

Detection and Monitoring of the Reporter

The accumulation of a reporter, such as green fluorescence, can be monitored by flow cytometry for transient transfections or by microscopy and plate readers for stable transfections. The latter instrumentation is commonly used in High Throughput Screening (HTS) and this assay is suitable for use in assays aimed at identifying compounds which alter the activity of the proteasome.

The use of fluorescent proteins to monitor the activity of the proteasome in high-throughput systems is an advantage over existing methods since it bypasses heavy biochemical manipulation and uses live cells that can be kept under culture for further investigation. The initial advantageous protein identified by the inventor as highly advantageous, ZsGreend410, appears to be the most sensitive fluorescent sensor of the activity of the proteasome described to date in the literature. (Bence et al., 2001; Dantuma et al., 2000; Nahreini et al., 2001; Andreatta et al., 2001). This preferred fusion protein construct is referred to as ZsGreend410.

The discovery of the reef coral fluorescent proteins (RCFPs) ZsGreen, ZsYellow, AmCyan, AsRed (red), DsRed (orange-red) and HcRed (far-red) has expanded the spectrum of colors available for studies of events in live cells (Matz et al., 1999; Gurskaya et al., 2001). It is an additional inventive proteasome sensor design approach to generate fusion proteins between the various RCFPs and various proteasome-targeting motifs or lysozyme targeting motifs. Once the fusion proteins are identified as targeted for degradation by the proteasome, cell lines expressing combinations of these various sensors of the activity of the proteasome can be produced to generate a "multiplexed" assay.

Sensitivity

The various design advancement of the present inventive proteasome sensor constructs of the present invention allow unprecedented sensitivity in proteasome activity detection. In determining sensitivity of his system, in the present application six hour after treating a cell with a proteasome modifying treatment is employed as a benchmark for sensitivity.

The present invention provides detection of Epoxomycin levels at about 1–30 nM, preferably about 1–10 nM, and most preferably about 1–5 nM are part of the present invention. Also, the present invention provides detection of Lactacystin at about 10–500 nM, preferably about 50–300 nM and most preferably about 100–200 nM. Further, the present invention provides detection of ZLLH at about 1–200 nM, preferably at about 5–50 nM, and most preferably at 10–20 nM. Additionally, the present invention provides detection of ALLN at about 0.05–2.5 uM, preferably 0.1–1.5 uM, and most preferably 0.2–1.0 uM.

Applications

High Throughput Screening Applications

Increases in fluorescence under conditions that alter the activity of the proteasome is substantially higher with the inventive constructs than with previously described fluorescent sensors of the activity of the proteasome. As a consequence, it is possible to analyze changes in fluorescence with instrumentations commonly used in high throughput screening. The use of such instrumentation has not been documented in studies using other sensors of the activity of the proteasome (Bence et al., 2001; Dantuma et al., 2000; Nahreini et al., 2001; Andreatta et al., 2001).

Previously described sensors have been limited to the use of EGFP not recognizing the special advantages of ZsGreen. Because the inventive improved construct design approach and component selection results in the increased sensitivity of the inventive sensor over the prior art proteasome sensors, the inventive constructs make high-throughput screen for proteasome activity available to pharmaceutical researchers for the first time.

In one preferred embodiment, mammalian cells are transfected with the plasmid. Under normal cell culture conditions, the fusion protein is rapidly degraded by the proteasome and the transfected cells show a fluorescence level close to the one of untransfected cells. In condition under which the ability of the proteasome to degrade proteins is altered (e.g. drug screening for a compound that modulate the activity of the proteasome, or a particular cellular state) ZsGreenld410 is no longer degraded and the cells accumulate green fluorescence.

In one application of the present invention to high throughput research tools, the accumulation of green fluorescence can be monitored by flow cytometry for transient transfections. Additional applications of the present invention to high throughput research tools include microscopy and plate readers for stable transfections.

The current inventive constructs allow an assay could be used in HTS aimed at identifying compounds which alter the activity of the proteasome. The need for such applications of proteasome sensors have previously been suggested by Dantuma et al. and by Andreatta et al. This research community recognized need is addressed by the present invention.

New Applications

The present invention allows for the first time a number of applications for proteasome sensors previously identified by the research community as important goals. However, the inventor has further identified original applications not previously conceived based on his unique inventive constructs While some examples of these unique applications follows, many other new applications are now also possible as enabled by the inventive constructs. Pharmaceutical screening applications are a particularly important focus for these applications.

Screening for Proteas me Targeting Motifs Inventive constructs based on new reporters such as ZsGreend410 can be used to screen for sequences within the genome that encode proteasome-targeting motifs. In one such assay, genomic sequences is inserted 3' of ZsGreen. The ability of this sequence to target ZsGreen for degradation by the proteasome will be investigated using two design criteria. First, the fluorescence of cells expressing the fusion protein should be lower than the one of cells expressing ZsGreen. Secondly, this fluorescence should increase in the presence of inhibitors of the activity of the proteasome.

Multiplexed Assays The discovery of the reef coral fluorescent proteins (RCFPs) ZsGreen, ZsYellow, AmCyan, AsRed (red), DsRed (orange-red) and HcRed (far-red) has expanded the spectrum of colors available for studies of events in live cells (Matz et al., 1999; Gurskaya et al., 2001).

According to the present invention, it would be advantageous to generate fusion proteins between the various RCFPs and various proteasome-targeting motifs. Once it is determined that these fusion proteins are targeted for degradation by the proteasome, cell lines expressing combinations of these various sensors of the activity of the proteasome are produced to generate a "multiplexed" assay.

Concomitant Assay for Proteasome and FP Effects. The inventive proteasome sensor can be used in combination with another fluorescent fusion protein to evaluate the effects of a given compound on both the proteasome and on the activity of the fluorescent fusion protein of interest. For example, inhibition of NF-kB is a major focus of interest in pharmaceutical companies for treatment of cancer and inflammatory diseases like rheumatoid arthritis. The activation of NF-kB follows degradation of the inhibitory molecule IkB and blocking IkB's degradation blocks NF-kB activation. If cells express both the proteasome sensor and a fluorescent IkB molecule (for e.g., fusion to DsRed or HcRed), one could screen for compound that inhibit IkB degradation (in red) without inhibiting the activity of the proteasome (in green). Other proteins of interest in the vein of IkB are: HIF, E1A, c-myc, p53, c-Fos, v-Myb, p730, HSP70, HMG-CoA reductase, TAT, alpha-casein, beta-casein, Cyclins A, B, D, E, CDK inhibitors, p53, c-fos, c-Jun, c-myc, N-myc, p130, cdc25 phosphatase, TAT, Topoisomerase I and lialpha.

Therefore, the present invention has new applications for such research needs as verify that a given compound doesn't act on the proteolytic activity of the proteasome, generating engineered plasmids encoding fusion proteins between fluorescent proteins and other proteasome-targeting motifs or lysozyme targeting motifs for a "multiplexed" assay, screening for sequences within the genome that encode proteasome-targeting motifs, and screening for compounds or sequences that affect the behavior of a protein of interest (fused to a reporter number 1) without affecting proteasome activity (monitored using the proteasome sensor).

As another example of the unique applications available with the present inventive construct, the study the role of various signal transduction pathways on the activity of the proteasome or study the status of the activity of the proteasome in various cell culture conditions (cell cycle, apoptosis, number of passages, adherent cells vs. suspension cells, cell migration, extra cellular matrix remodeling, etc.)

Analysis of End Proteolitic Systems

One of the applications of the present invention allows, for the first time, the in vivo analysis of both proteasome dependent proteolysis and other proteolytic system, such as the endoproteolytic systems. A particularly avantagouse application for this aspect of the invention is to screen for compounds which inhibit enzymes involved with the endoproteolytic processes.

A sequence X is cloned between ZsGreen coding sequence and D410 destabilization motif coding sequence. The endoproteolytic cleavage of X is monitored using ZsGreen florescence. For example, a sequence X encoding a caspase cleavage site is inserted between the two above sequences.

The plasmid coding for these fusion proteins is transfected in cells and the resulting fusion protein is expressed. Under conditions where the caspase is inactive or unable to perform its endoproteolytic activity, the fusion protein is constantly degraded by the proteasome and as a result, the florescence is low. When the caspase becomes active, it will cleave the sequence X, thereby disconnecting the D410 sequence from the florescent reporter. As a consequence, the florescence in the cell will increase.

EXPERIMENTAL

Method and Approach in Generating Preferred Embodiment

In order to generate a most sensitive fluorescent reporter of the activity of the proteasome, the inventor determined to take advantage of the newly discovered RCFP ZsGreen and investigated the ability of motifs from MODC to target ZsGreen for degradation by the proteasome. The inventors generated a fusion protein between ZsGreen and a proteasome targeting motif corresponding to amino-acids 410 to 461 of MODC: ZsGreend410. Cells expressing this fusion protein have a very low fluorescence in normal cell culture conditions. This low fluorescence is due to constitutive degradation by the proteasome since a sharp increase in fluorescence is observed under conditions which inhibit the activity of the proteasome. Hence, ZsGreend410 can be used as a sensor of the activity of the proteasome. The increase in fluorescence can be monitored by flow cytometry in transient transfections. The inventor generated a stable cell clone expressing ZsGreend410. The inventor show that increase of fluorescence of this clone can be monitored by flow cytometry, microscopy or using a 96 well plate reader. The latter instrumentation is commonly used in high throughput screening and the inventor conclude that ZsGreend410 could be used to identify compounds that alter the activity of the proteasome in a high throughput fashion.

Engineered plasmids encoding fusion proteins between ZsGreen and other proteasome-targeting motifs yield sensors of the proteasome that have a high sensitivity.

Definitions:
1-ZsGreenwt or wt ZsGreen: zFP506 (Matz et al., 1999)
2-d410: Mouse Ornithine Decarboxylase sequence from aa 410–461
3-ZsGreend410=fusion between wt ZsGreen and d410

Preferred Embodiment

In the preferred embodiment set out in FIG. 2, the use of ZsGreend410 is employed as a sensor of the activity of the Proteasome. Simply, ZsGreend410 consists of the fusion of a fluorescent protein to a sequence that is a fragment of a protein that normally occurs in mammalian cells and has been shown to be a substrate of the proteasome (mouse ornithine decarboxylase).

EXAMPLE 1

[FIG. 1] In order to convert ZsGreen into a substrate for proteasomal degradation and to use it as a sensor of the activity of the proteasome, the inventor generated 2 plasmids encoding fusion proteins between ZsGreen and sequences derived from MODC, ZsGreendl and ZsGreend410 (FIG. 1). The d1 sequence is derived from amino acid 422 to 461 of MODC: it encompasses the PEST motifs and has been mutated to even decrease the stability of EGFP (Li et al., 1998). EGFPd1 fusion protein has a half-life of 50 minutes compared to around 26 hours for EGFP (Corish and Tyler-Smith, 1999). The d410 sequence corresponds to amino-acid 410 to 461 and its ability to destabilized fluorescent proteins has not been assessed. However, data from Li and Coffino suggest that this sequence is likely to be a stronger proteasome-targeting motif than the d2 and d1 sequences (Li and Coffino, 1993)

EXAMPLE 2

(FIGS. 2A&B) To establish if the above proteins are substrate for degradation by the proteasome, HEK 293 cells were transiently transfected with the plasmids and the mean fluorescence intensity (MFI) of the cells was measured by flow cytometry 16 hours after transfection. As can be seen on FIG. 2A, ZsGreen-expressing cells harbor a strong fluorescence. The MFI of cells transfected with the plasmid encoding ZsGreendl is 4 times weaker. The MFI of the cells transfected with pZsGreend410 is marginally above the fluorescence of non-transfected cells. The low fluorescence of ZsGreendl expressing cells is in line with the reported efficiency of the d1 degradation signal and the very low fluorescence of cells transfected with the ZsGreend410-encoding plasmid suggest that the d410 motif is an even stronger destabilization motif (Li et al., 1998). Alternatively, the fusion of ZsGreen to the d1 and d410 domains could result in proteins with decreased intrinsic fluorescence. To distinguish between these two possibilities, the transiently transfected cells were treated with ALLN, a well-characterized reversible inhibitor of proteasomal degradation. As seen on FIG. 2B, ALLN treatment only marginally increases the fluorescence of ZsGreen expressing cells whereas the fluorescence of pZsGreendl and pZsGreend410-transfected cells increased in a time-dependent fashion. Similar results were obtained using another inhibitor of proteasomal degradation, Lactacystin or in HeLa cells (not shown). These increases in fluorescence are inversely proportional to the level of fluorescence in untreated cells and show that the low MFI of ZsGreendl and ZsGreend410 expressing cells is primarily due to their targeting for proteasomal degradation. The previously uncharacterized d410 domain is therefore a very strong destabilization motif. The increase in fluorescence of ZsGreend410-expressing cells upon proteasome inhibition is stronger than the one observed with previously described destabilized fluorescent proteins and ZsGreend410 is one of the most sensitive sensor of the activity of the proteasome described thus far (data not shown). It is likely due to both the strong brightness of ZsGreen and the nature of the d410 motif. More experiments will be needed to understand the critical residues in the d410 motif responsible for proteasome-targeting.

EXAMPLE 3

Figure 2B:
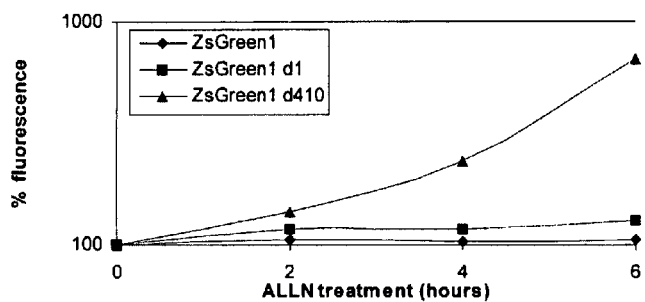
FIG. 2B ALLN treatment effects on fluorescence of ZsGreen, pZsGreend1 and pZsGreend410 expressing cells (transient transfection).
Figure 3C:
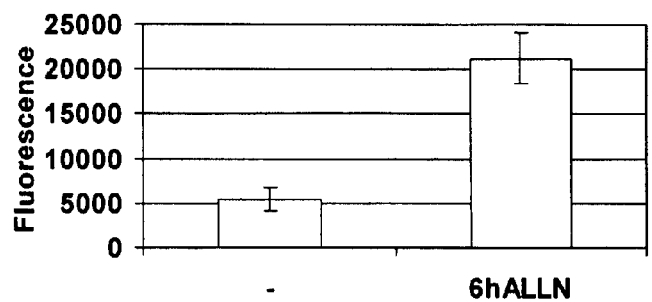
FIG. 3A, B and C: Photographs of florescent levels of non-transfected cells and cells transfected with ZsGreend410 with or without ALLN treatment (stable transfection).

(FIG. 3) In order to develop a cell-based assay for High-Throughput Screening (HTS) using ZsGreend410, we next generated stable transfectant expressing the ZsGreend410. Since flow cytometry is more sensitive than most of the methods used in HTS, we needed to generate clones with a high basal fluorescence and strong increases in fluorescence upon proteasome inhibition. We selected stable HEK 293 clones from a stably transfected population after a 4-hour treatment with ALLN and sorted the cells in the population with the highest MFI (500 to 10000). The clones were maintained in culture for several weeks before analysis. As illustrated in FIG. 3A, the fluorescence of cells stably expressing ZsGreend410 is above the one of non-transfected cells and above the one of cells transiently transfected with pZsGreend410. This fluorescence sharply increases upon treatment with ALLN. Comparison of FIGS. 2B and 3A shows that the cloning strategy allowed us to generate an assay with a higher basal fluorescence and fluorescence increases upon proteasome inhibition 5 to 10 times higher than in transient transfection. On FIG. 3B ALLN-treated and non-treated clones were observed by microscopy. Several other clones gave similar results (data not shown). In order to investigate if the assay could be used in a HTS fashion the clone was grown in 96 well plates and the fluorescence of non-treated or ALLN-treated cells was observed using a fluorescence reader, a commonly used instrumentation for HTS. As can be seen on FIG. 3C, the assay is sensitive enough for changes in fluorescence to be observed using a fluorescence analysis station and can be used in a high-throughput fashion.

1. Nahreini P, Andreatta C, Prasad K N. Proteasome activity is critical for the cAMP-induced differentiation of neuroblastoma cells. *Cell Mol Neurobiol.* 2001 October;21(5): 509–21.
2. Andreatta C, Nahreini P, Hovland A R, Kumar B, Edwards-Prasad J, Prasad K N. Use of short-lived green fluorescent protein for the detection of proteasome inhibition. *Biotechniques.* 2001 March;30(3):656–60.
3. Dantuma N P, Lindsten K, Glas R, Jellne M, Masucci M G. Short-lived green fluorescent proteins for quantifying ubiquitin/proteasome-dependent proteolysis in living cells. *Nat Biotechnol.* 2000 May; 18(5):538–43.
4. Bence N F, Sampat R M, Kopito R R. Impairment of the ubiquitin-proteasome system by protein aggregation. *Science.* 2001 May 25;292(5521):1552–5.
5. Meng L, Mohan R, Kwok B H, Elofsson M, Sin N, Crews C M. Epoxomicin, a potent and selective proteasome inhibitor, exhibits in vivo antiinflammatory activity. *Proc Nal Acad Sci USA.* 96(18):10403–8 (1999).
6. Schwartz A L, Ciechanover A. The ubiquitin-proteasome pathway and pathogenesis of human diseases. *Annu Rev Med.* 50:57–74 (1999).
7. Adams J. Proteasome inhibition: a novel approach to cancer therapy. *Trends Mol Med.* 2002;8(4 Suppl): S49–54.
8. Li X, Zhao X, Fang Y, Jiang X, Duong T, Fan C, Huang C C, Kain S R. Generation of destabilized green fluorescent protein as a transcription reporter. *J Biol Chem.* 1998 Dec. 25;273(52):34970–5.
9. Corish P, Tyler-Smith C. Attenuation of green fluorescent protein half-life in mammalian cells. *Protein Eng.* 1999 December; 12(12):1035–40.
10. Loetscher P, Pratt G, Rechsteiner M. The C terminus of mouse ornithine decarboxylase confers rapid degradation on dihydrofolate reductase. Support for the pest hypothesis. *J Biol Chem.* 1991 Jun. 15;266(17):11213–20.
11. Rogers S, Wells R, Rechsteiner M. Amino acid sequences common to rapidly degraded proteins: the PEST hypothesis. *Science.* 1986 Oct 17;234(4774):364–8.
12. Ghoda L, Sidney D, Macrae M, Coffino P. Structural elements of ornithine decarboxylase required for intracellular degradation and polyamine-dependent regulation. *Mol Cell Biol.* 1992 May;12(5):2178–85.
13. Gurskaya N G, Fradkov A F, Terskikh A, Matz M V, Labas Y A, Martynov V I, Yanushevich Y G, Lukyanov K A, Lukyanov S A. GFP-like chromoproteins as a source of far-red fluorescent proteins. FEBS Lett. 2001 Oct 19; 507(1): 16–20.
14. Matz M V, Fradkov A F, Labas Y A, Savitsky A P, Zaraisky A G, Markelov M L, Lukyanov S A. Fluorescent proteins from nonbioluminescent Anthozoa species. *Nat Biotechnol.* 1999 Oct; 17(10):969–73.
15. Li X, Coffino P. Degradation of ornithine decarboxylase: exposure of the C-terminal target by a polyamine-inducible inhibitory protein. *Mol Cell Biol.* 1993 April;13(4): 2377–83.

RELATED BD PATENTS AND PATENT APPLICATIONS

U.S. Pat. No. 6,306,600 Kain et al.
U.S. Pat. No. 6,130,313 Li et al.

The invention claimed is:

1. A nucleic acid which encodes a fusion protein comprising:
   a) a reef coral fluorescent protein reporter domain, and
   b) a protein degradation domain, wherein said protein degradation domain comprises:
      i) a PEST targeting sequence; and
      ii) at least one flanking sequence N-terminal of the PEST
      sequence comprising from about 5 to about 50 residues; and
   wherein said fusion protein is at least 4 times more sensitive as a reporter of proteasome inhibition than a fusion protein that includes a d1 protein degradation domain.

2. The nucleic acid of claim 1, wherein said PEST targeting sequence is a MODC PEST targeting sequence.

3. The nucleic acid of claim 2, wherein said PEST targeting sequence consists of amino acids 422–461 of MODC.

4. The nucleic acid of claim 1, wherein said targeting sequence comprises aa 410 to 461 of MODC.

5. The nucleic acid of claim 1, wherein said nucleic acid is a DNA.

6. The nucleic acid of claim 1, wherein said nucleic acid is provided in a vector.

7. The nucleic acid of claim 6, wherein said vector is a plasmid or viral vector.

8. The nucleic acid of claim 1, wherein said nucleic acid is a RNA.

9. The nucleic acid of claim 1, wherein said reef coral fluorescent protein is selected from the group consisting of: ZsGreen, ZsYellow, AmCyan, AsRed, DsRed and HcRed.

10. The nucleic acid of claim 1 wherein said reporter domain is ZsGreen.

11. A fusion protein encoded by the nucleic acid of claim 1.

12. A transgenic cell or the progeny thereof comprising the nucleic acid of claim 1.

13. A method of evaluating proteasome activity in a cell, said method comprising:
   introducing into said cell a nucleic acid according to claim 1 or a protein encoded thereby; and
   detecting the presence of reporter activity in said cell to assess proteasome activity in said cell.

14. The method of claim 13, wherein said method comprises introducing said fusion protein into said cell.

15. The method of claim 13, wherein said method comprises introducing said nucleic acid into said cell.

16. The method of claim 13, further comprising contacting said cell with an agent prior to said detecting.

17. The method of claim 13, further wherein said detecting comprises using flow cytometry or microscopy.

18. The method of claim 13, further comprising introducing into said cell a nucleic acid encoding a fusion protein comprising:
   a fluorescent protein reporter domain and
   a protein of interest.

19. The method of claim 13, further comprising introducing into said cell a nucleic acid encoding a fusion protein comprising:
   a fluorescent protein reporter domain and
   a second protein degradation domain.

* * * * *